(12) United States Patent
Dixon et al.

(10) Patent No.: US 6,682,530 B2
(45) Date of Patent: Jan. 27, 2004

(54) DYNAMIZED VERTEBRAL STABILIZER USING AN OUTRIGGER IMPLANT

(76) Inventors: Robert A Dixon, 10577 Durham Pl., Powell, OH (US) 43065; Donald J Hackman, 3499 Kirkham Rd., Columbus, OH (US) 43221

( * ) Notice: Subject to any disclaimer, the term of this patent is extended or adjusted under 35 U.S.C. 154(b) by 40 days.

(21) Appl. No.: 10/340,967

(22) Filed: Jan. 13, 2003

(65) Prior Publication Data

US 2003/0135210 A1 Jul. 17, 2003

Related U.S. Application Data

(60) Provisional application No. 60/348,180, filed on Jan. 14, 2002.

(51) Int. Cl.$^7$ .............................................. A61B 17/70
(52) U.S. Cl. ........................................ 606/61; 606/70
(58) Field of Search .............................. 606/60, 61, 69, 606/70

(56) References Cited

U.S. PATENT DOCUMENTS

| | | | | | |
|---|---|---|---|---|---|
| 4,790,297 | A | * | 12/1988 | Luque | 606/61 |
| 5,290,288 | A | * | 3/1994 | Vignaud et al. | 606/61 |
| 6,176,861 | B1 | * | 1/2001 | Bernstein et al. | 606/61 |
| 2002/0029040 | A1 | * | 3/2002 | Morrison et al. | 606/61 |
| 2003/0045875 | A1 | * | 3/2003 | Bertranou et al. | 606/61 |

* cited by examiner

*Primary Examiner*—Kevin Shaver
*Assistant Examiner*—Michael B. Priddy

(57) ABSTRACT

A device and a method for stabilizing lumbar and thoracic vertebra or individual bones in human spine or bone column is provided for the purpose of fixing a vertebra or individual bone with respect to other vertebra or individual bones and with respect to other parts of the spinal or bone column. While providing spinal stabilization, the stabilizer allows axial load sharing or construct dynamized action. The device allows the vertebra or individual bones to be held in compression allowing subsidence along the plate axis or to be fixed with respect to the plate for rigid stabilization. The vertebra or individual bones will be prevented from distraction by a stop lock clamp. The device may be configured as a fully or partially rigid system.

7 Claims, 4 Drawing Sheets

DYNAMIZED VERTEBRAL STABILIZER USING AN OUTRIGGER IMPLANT

CROSS-REFERENCE TO RELATED APPLICATIONS

This patent claims the benefit of U.S. provisional application Ser. No. 60/348,180 filed on Jan. 14, 2002

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

This invention relates to implant assemblies for use in stabilizing bone members to treat patients with ruptured or degenerated intervertebral bone discs and to replace vertebrae or individual bone bodies damaged by fracture, tumor or degenerative processes. Specifically, the invention relates to dynamized vertebral or individual bone implants and methods of implanting them to form a support in the spinal column or bone column and to promote fusion, healing, and bone growth in the human spine or bone column, incorporating an elongated member such as a plate.

BACKGROUND OF THE INVENTION

When surgery is needed, the discs are removed and replaced with grafts that will heal or fuse with the vertebra or individual bones. This implanted graft provides realignment and stabilization while healing takes place. Those surgeries that use implanted stabilizers, along with a graft are more successful than those that do not use a stabilizer. Surgeries that maintain compression between the vertebra or individual bones during healing are the most successful.

Devices that support all of the vertebra or individual bone's force leaving no force on the intervertebral or individual bone's graft are called "stress shielding" devices. Devices that support or share a portion of the spinal load in parallel with the graft are called "load sharing" devices. Devices that allow axial subsidence of the implant and support most of the load on the individual bone grafts are referred to as providing "dynamized" action.

The present invention allows the surgeon to select any of these three conditions at the time of surgery, by selecting the bone screw nut and positioning the stop Lock clamp. The present patent will restrict distraction, lateral translation, and rotational shear, reducing the stretching rupture and shear tearing of the forming nutrient blood vessels while allowing compression during the healing process.

SUMMARY OF THE INVENTION

The present patent relates to a spinal stabilizing device, and a method of implanting it on the posterior, or lateral side of the human spine or bone column. This device includes a rectangular shaped plate to allow axial subsiding motion without rotation or shear translation. The plate is for placement adjacent to and along the spinal or bone column, and having a longitudinal axis. The plate includes an open slot substantially parallel to the plate axis extending substantially the entire longitudinal dimension of the plate, leaving the plate ends the same thickness as the plate rails. The plate is raised above the individual bones by the thickness of a bone screw driving portion and the thickness of a plate guide. The stabilizer further includes a plate guide with two tubes attached to the plate guide and extending perpendicular to the plane of the plate guide and having inner diameters which slidably engage machine screws and outer diameters which will slidably engage the plate slot. The plate guide also including an "L" shaped extension, referred to as the outrigger arm extending perpendicular to and in the plane of the plate guide anteriorly, for placement of an anterior bone screw which is fixed to the plate guide through a locking means. This system also includes a bone screw having a bone threaded portion which engages the bone, a driving portion, and a machine thread stud portion extending through the plate guide tubes, so that the screw's driving portion abuts the vertebra or individual bones, and the machine thread portion engages the tubes and protrudes above the tubes. Also provided are two different nuts with a threaded hole extending through the body portion for threaded engagement with the machine threaded portion and a flange substantially concentric with the nut's thread. One nut includes an undercut and is referred to as a clamp nut, the second nut, which does not have an undercut, is referred to as a sliding nut. If a sliding nut is used it will clamp against the tube, leaving clearance between the plate and the plate guide allowing for dynamized motion. If a clamp nut is used, the nut will not contact the Tube, but will clamp the plate to the plate guide for rigid clamping. At the time of implantation the device is adapted to either rigidly fix the vertebra or individual bones or to allow selected axial subsiding action. Stop Lock clamps are provided to control the displacement of the plate with respect to the plate guides and to add torsional rigidity to the implant and improve pullout resistance by virtue of its orientation relative to the Posterior Bone Screws.

BRIEF DESCRIPTION OF THE DRAWINGS

Other features, advantages, and objects will be evident from the following specification.

FIG. 7a is an enlarged view of FIG. 6a.

FIG. 8b is an enlarged view of FIG. 8a.

DETAILED DESCRIPTION OF THE INVENTION

For the transfer of knowledge and an understanding of the principles of the present invention, the illustrated drawings and the specifications referenced will describe one specific size and embodiment of a working model of the dynamized stabilizer, which has been constructed for demonstration and reduction to practice. It will be understood that no limitation of the scope of the invention is intended. These specifications contain an organized, written description of the invention, and of the manner and process of making and using it. It is presented in such full, clear, concise, and exact terms as to enable any person skilled in the art of manufacturing and implantation of medical devices to make and use the stabilizer described in the best mode contemplated by the inventors.

The best mode material for the stabilizer is titanium alloy Ti-6AI-4V. It is the most bio-compatable of all metals due to its total resistance to attack by human and animal body's. It also has high strength, low density, flexibility, low modulus of elasticity, and a low thermal coefficient of expansion. Other advantages of this material are its decreased interference with metal detectors and with magnetic resonance imaging (MRI) used for postoperative evaluation. Ti-6AI-4V is best in the alpha-beta phase, which can be heat-treated to obtain the desired properties. Details of the fabrication methods and dimensions of the model are given in the section titled Dynamized Bone Stabilizer Manufacturing Method.

Figure 1:
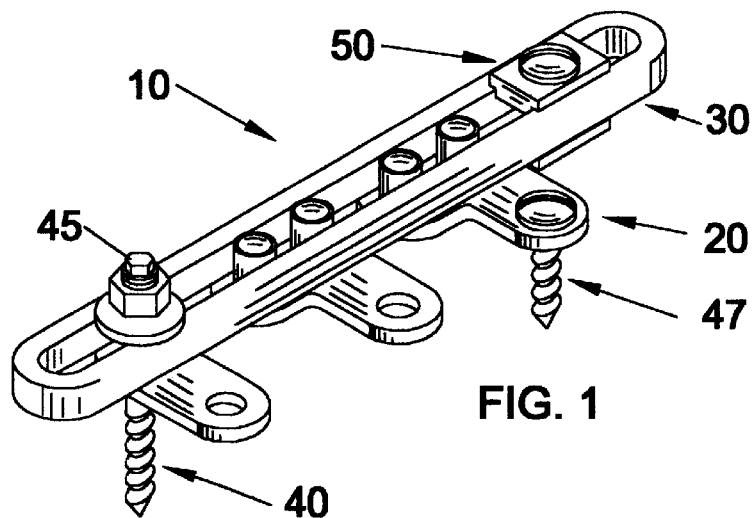
FIG. 1 is an isometric view of a two-level dynamized spinal stabilization system.

The invention will be presented in these specifications in the following order:

The Dynamized Spinal Stabilization System 10.
The Plate Guide 20, Including The Guide Tubes 22, And The Outrigger Arm 28,
The Plate 30. With The Slot 34.
The Bone Screws 40. Including The Bone Thread End 42, The Drive Feature 44, And The Machine Threaded Stud Portion 46.
Dynamizing And Rigidizing Action including: The Sliding Nut 48 And The Clamp Nut 49.
The Clamp Nut and the Sliding Nut.
Stop Lock clamps 50
The Graft 62.
Dynamized Bone Stabilizer Manufacturing Method.
Dynamized Bone Stabilizer Implanting Method The Dynamized Spinal Stabilization System
Referring generally to FIGS. 1, 2, and 3, one embodiment of the dynamized stabilizer implant system 10 of the present patent is illustrated. The system is implanted on vertebra or individual bones 60 on the spinal or bone column 61. In this embodiment the system 10 includes a bone plate 30 having a longitudinal axis 31 substantially parallel to the spinal or bone column axis 63, a plate guide 20 with two tubes 22, an outrigger arm 38, an anterior screw 47, a bone screw 40, two different nuts 48 and 49, and a graft 62. Also included is a stop lock clamp 50 including an upper clamp 52, a lower clamp 54, and a stop screw 56.

Figure 2:
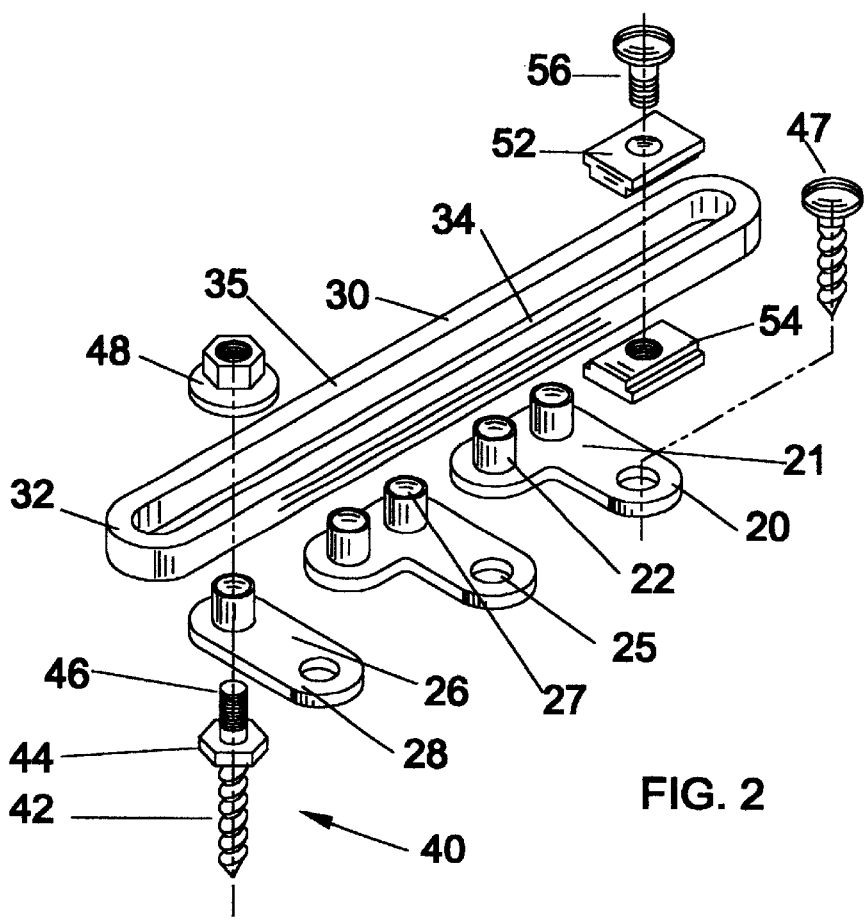
FIG. 2 is an isometric exploded view of a two-level dynamized spinal stabilization system.
Figure 3:
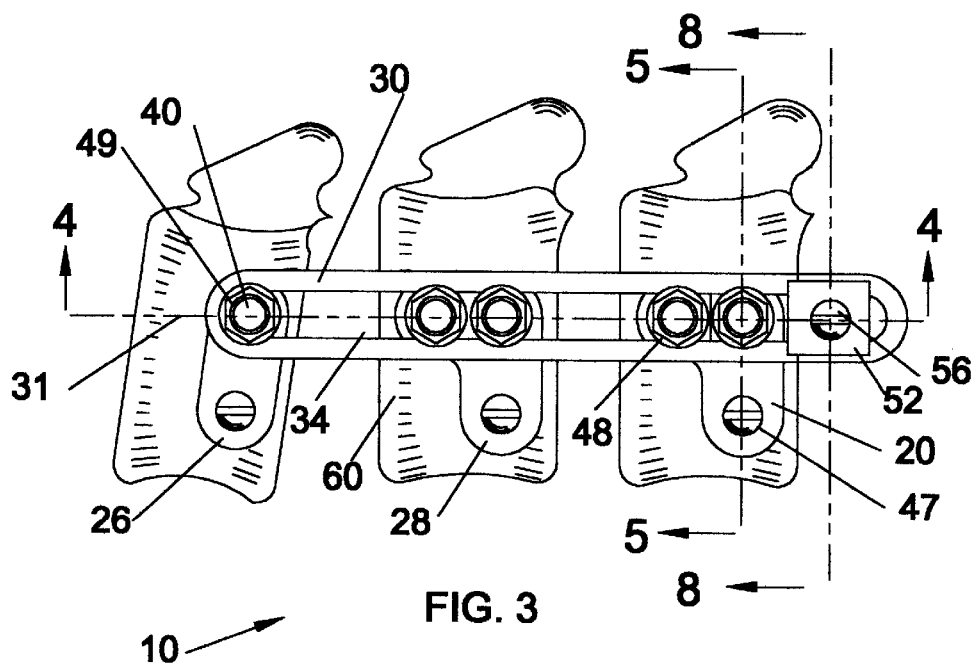
FIG. 3 is a lateral view of a two-level dynamized spinal stabilization system with a lateral attachment to lumbar vertebra or individual bones.
Figure 4:
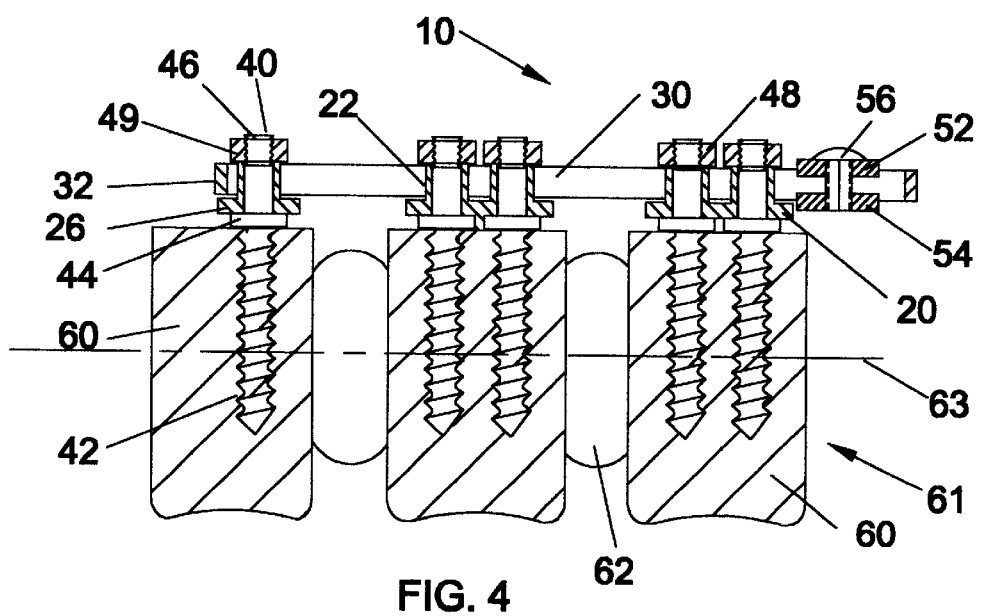
FIG. 4 is an anterior cross-sectional view of a two-level dynamized spinal stabilization system with a lateral attachment to lumbar vertebra or individual bones and Bone Screws through the vertebra or individual bones, taken along the line 4—4 of FIG. 3

The Plate Guide
Referring generally to FIGS. 2, 3, and 4 the plate guide 20 is an "L" shaped plate, the top face of the plate guide surface 21 interfaces the lower face of the plate 30 and the plate guide tube 22 outer diameter interfaces with the plate slot 34 sides. When the plate guide is clamped, the interface surfaces are static. When the device is free the interface is dynamic sliding. Sliding does not allow rotation or horizontal translation of the plate relative to the vertebrae or individual bones, This device will allow axial sliding of the bone screws 40 and plate guides 20.

The plate guide 20 has two tubes 22 fixed to it and extending perpendicular outward from the plane of the plate guide. The two fixed guide tubes 22 prevent plate 30 rotation and lateral sliding. The guide tubes give guidance to plate 30 through plate slot 34. The tubes have through holes 27 that allow the bone screw machine threads 46 to protrude above the top of the tubes. The inner diameters of the tubes slidably engage and interface with the machine threaded stud portion 46 of the bone screw 40. The tube length protrusion shown as 70 in FIG. 7a prevents the sliding nut 48 from direct plate to plate guide clamping by restricting the sliding nut from compressing the plate.

The outrigger arm 28 of the plate guide 20 comprises a contiguous metal piece curved 23 to fit the lateral or anterior curvature of the vertebral body 60. An anterior (ventral) bone screw 47 clearance hole 25 and one or more spikes 29, shown in FIG. 9b, on the lower surface fixes the outrigger arm 28 into place.

Figure 9A:
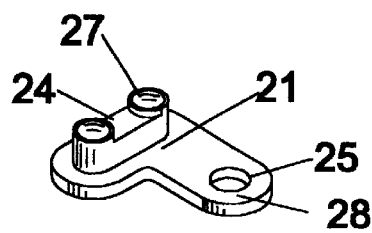
FIG. 9a is an isometric view of a plate guide with an optional boss.
Figure 9B:
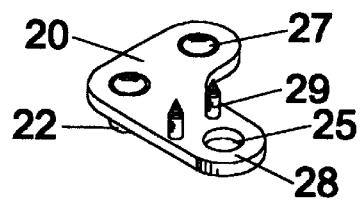
FIG. 9b is an isometric view of the bottom of a plate guide showing two spikes.

The outrigger arm 28 extends perpendicular to and substantially in the plane of the plate guide 20 anteriorly, for placement of an anterior bone screw 47 which is fixed to the plate guide through a locking means. The anterior bone screw serves to provide rotational, and pullout resistance to the plate guides. An optional malleable portion in the plate guide arm between the posterior bone screws 40 and the anterior bone screw 47 to allow the outrigger arm 28, to better conform to the vertebra or the individual bone's curve. An additional two-hole plate guide 26, shown in FIG. 3 allows the plate guide to be set at an angle with the plate 30. In another embodiment the plate may have an integral boss 24, with drilled holes in place of the tubes 22, as shown in FIG. 9a. The spikes 29, shown in FIG. 9b, are driven into the vertebra or individual bones stabilizing the outrigger arm 28 prior to or during bone screw placement.

Figure 6A:
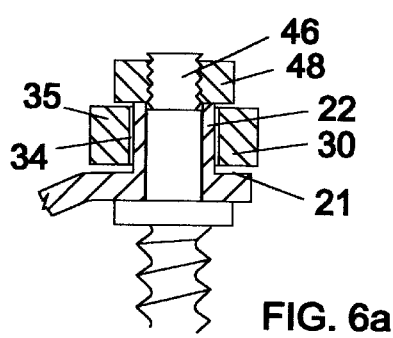
FIG. 6a is an enlarged axial cross-sectional view of the circled area of FIG. 5 showing a sliding nut.

The Plate
Referring generally to FIG. 2 the plate 30 has a rectangular cross section with a slot 34 creating two rails 35, shown in the section view of FIG. 6a. The plate end 32 is semicircular with rounded ends and a width equal to that of the plate rail. The plate lower face interfaces with the plate guide's upper surface 21. The plate upper face interfaces with the nut flange 57. The plate also has two substantially parallel side faces with a thickness of sufficient strength to substantially eliminate bending. The plate 30 is machined from a single piece of titanium. It has an through guide Slot 34 parallel to its longitudinal axis 31 to receive and contain the tube portion 22 of the plate guide 20. Unlike stabilizing plates with preformed holes that dictate the location of the bone screws 40, this plate allows the bone screws 40 to be infinitely positioned axially to place the bone screws into the desired position of the vertebra or individual bones 60. The plate may be bent 23 at the time of manufacture or at the time of surgery to accommodate spinal curvatures.

Figure 5:
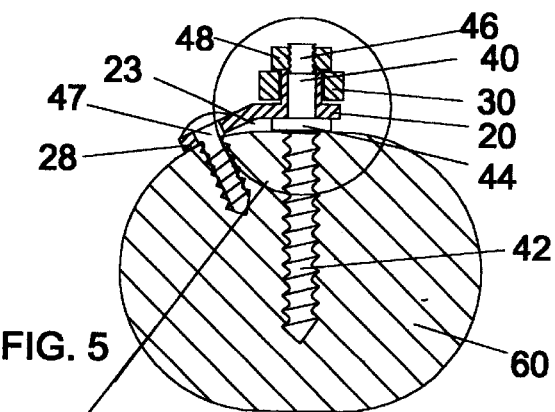
FIG. 5 is an axial cross-sectional view of a dynamized spinal stabilization system, taken along the line 5—5 of FIG. 3.

The Bone Screws
Referring generally to FIGS. 2, 4, and 5, the bone screw 40, having a bone threaded portion 42 which engages the bone 60, a driving portion 44 with a hexagonal head, a machine threaded stud portion 46, which is not threaded at the tube/stud interface, and a top drive feature 45. The bone screw portion is threaded into the bone in pairs with the screw's centerline distance equal to the guide plate tubes centerline distance. The bone screws 40 are driven in to the bone until the screw's driving portion 44 abuts the vertebra or individual bones. All or some of the bone screws may be self-tapping. The machine threads extend above the plate guide tube 22 so that the nuts 48 and 49 can have threaded engagement and interface with the screw machine thread portion. Two different nuts with threaded holes and flanges 57 as shown in FIGS. 6a, 6b, 7a, and 7b are provided. For final adjustment after implantation the final height is adjusted using the top drive feature.

Dynamizing and Rigidizing Action

Figure 7A:
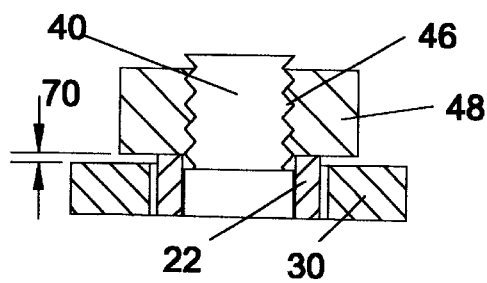
Figure 6B:
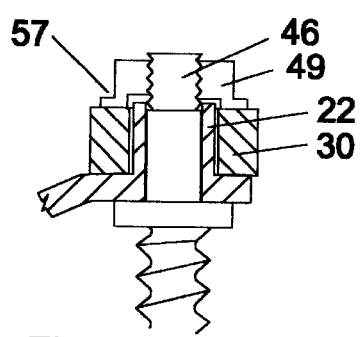
FIG. 6b is an enlarged axial cross-section view of the circled area of FIG. 5 showing a dynamized spinal stabilization system with a clamping nut.
Figure 7B:
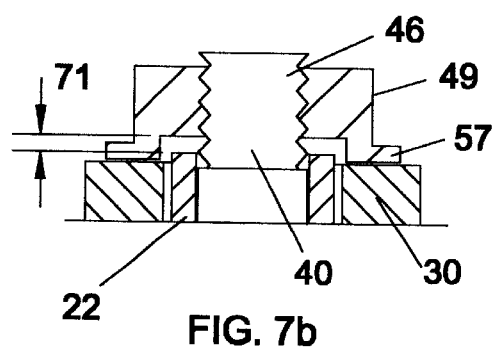
FIG. 7b is an enlarged view of FIG. 6b.

Referring generally to FIGS. 7a, and 7b, in the dynamized installation the sliding nut 48 clamps tight against the end of guide tube 22 allowing clearance 70, shown in FIG. 7a, between the plate 30 and the plate guide 20. The guide tubes 22 diameters are smaller then the plate slot 34 width to maintain clearance between the plate slot and the tube. Installing sliding nuts 48 will allow the plate 30 to slide relative to the plate guide 20.

In a rigid installation the clamping nut 49, shown in FIG. 7b, is undercut with a clearance 71 preventing the nut from clamping against the tube 22. This clamping forces the plate 30 against the plate guide 20 clamping them together rigidly to preventing relative motion between the plate and the plate guide. Installing the clamp nut 49 will prevent motion between the plate and the plate guide.

In the preferred embodiment sliding or rigidity can be selected or changed by the specific nut, 48 or 49. Because of the metal-to-metal clamping with either nut there is no need for additional nut locking devices.

The Clamp Nut and The Sliding Nut

Figure 8A:
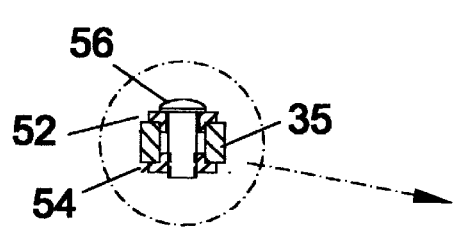
FIG. 8a is an axial cross-sectional view of a stop lock clamp, taken along the line 8—8 of FIG. 3.
Figure 8B:
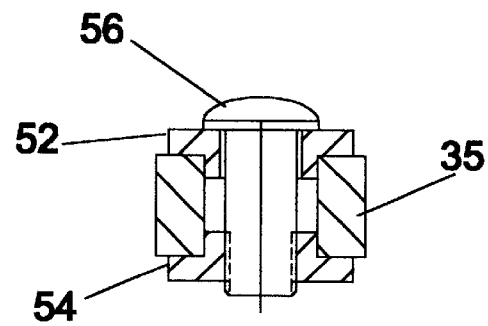
Figure 7C:
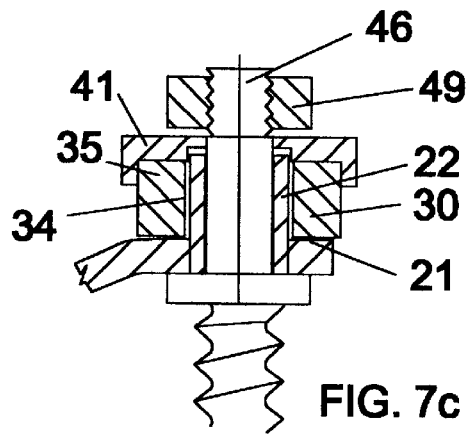
FIG. 7c is an enlarged view of FIG. 5 showing an upper saddle clamp.

Referring generally to FIGS. 1, 2, 4, 7a, and 7b. The nuts consist of a hexagonal portion and a flange portion 57 and an internal thread. The nut flange interfaces with the plate 30 upper face and the nut threaded portion interfaces with the machine threaded stud portion 46. The sliding nut 48 also interfaces with the top of the guide tube 22 and dynamically sliding with the plate upper face. The clamp nut 49 interfaces statically clamped with the plate upper face. The clamp nut 49 has an undercut that clears the tube 22 top allowing the nut to clamp the plate 30 directly to the plate guide 20 thereby rigidizing the vertebra or individual bones 60. Because of the metal-to-metal clamping of the sliding nut 48 and the guide tube; and the metal to metal clamping of the clamp nut 49 to the plate the nuts do not require anti-rotational locks, such as auxiliary screw connectors, cams, wedges or locking caps. The plate heights are adjusted by rotateing the bone screw with a driving wrench on the top drive An optional upper saddle clamp 41, shown in FIG. 8b, may be used with the clamp nut 49 for additional rigidity between the bone screw 40 and the plate 30. The saddle clamp has flanges which trap the plate rails from spreading. The metal-to-metal clamping of the bone screw 40 to the Plate 30 provides a fully rigid bone stabilizer system.

Stop Lock Clamps

Figure 8C:
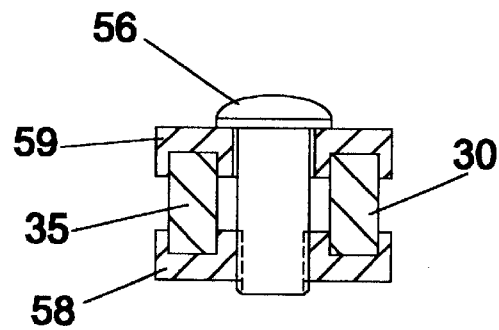
FIG. 8c is a view of FIG. 8b showing an upper and lower stop lock saddle clamp

Referring generally to FIGS. 2, 4, 8a, and 8b, the stop lock clamp assembly 50 is a clamp consisting of an upper clamp 52, a lower clamp 54, and a screw 56 that pulls the upper and lower clamps against the plate 30. This rigid clamp will prevent or stop the plate guide 20 from distracting yet will allow it to freely subside, maintaining compression between the vertebra or individual bones 60 and the graft 62 to allow for any graft resorbtion and settling. The stop lock clamp will also increase plate rigidity and serve as a travel limit stop for the bone screw 40/plate guide 20 assembly with respect to the plate 30. The graft should be compressed before tightening the lock clamp screw 56. An optional upper stop lock saddle clamp 59 and a lower stop lock saddle clamp 58, shown FIG. 8c, will add rigidity to the system 10 and will prevent the plate slot from widening.

The Graft

Referring generally to FIG. 4, for consistency in this patent the word stabilizer or implant refer to the plate-screw assembly 10, whereas the word graft 62 refers to the interbody material replacing the removed disc or vertebra. The graft is pieces of human bone, a piece of calcium, a synthetic material, a protein/DNA/gene sequence, or a metal device. These devices act as a bone growth enhancer and share the vertebra or individual bone's load to maintain the disc space along with the stabilization system of the present invention. The graft must maintain its height until the healing is complete. The plate 30 must also help to keep the graft in place. The vertebra or individual bone's end plates are cartilage, which must be removed so the graft has live healthy bone to grow with. An expandable interbody can be used to initially compress the construct.

Dynamized Bone Stabilizer Manufacturing Method

The components are made of titanium alloy Ti-AI6-V4. They are machined from rod and bar stock. Ti-AI6-V4 can be machined by the customary methods. However it requires slow speeds, heavy feeds to reduce work hardening, and an ample supply of coolant. Because heavy feeds create large loads on the tool bits, the machine tools and setups must be very rigid to avoid chattering. The tool bits must remain sharp therefor carbide tool bits are recommended. Ti-AI6-V4 can be welded only in a clean inert atmosphere. The recommended welding process is TIG (Tungsten electrode Inert Gas).

A recommended titanium supplier is Tico Titanium, inc. Tyco can furnish bar and rod stock or near net cut titanium shapes with excellent edge finish and a high degree of intricacy or size tolerance using abrasive water-jet cutting systems operated by CAD systems. Water-Jet cut titanium materials are preferred because the cold cutting process does not change the properties of the material.

The dimensions of the working model are described below. It will be understood that no limitation of the scope of the invention is intended by these specifications.

The plate is 4.5 mm (0.187 inch) thick, 12.7 mm (0.500 inch) wide, and 108 mm (4.25 inch) long.

The plate slot is 6.5 mm (0.255 inch) wide.

The guide plate is 2.5 mm (0.100 inch) thick, 22.8 mm (0.900 inch) long, and 12.7 mm (0.500 inch) wide.

The guide plate tubes are 6.3 mm (0.250 inch) outer diameter, 4.83 mm (0.190 inch) inner diameter, and 5 mm (0.200 inch) long.

The outrigger is 2.5 mm (0.100 inch) thick, 5 mm (0.200 inch) wide, and 15 mm (0.600 inch) long.

The bone screw is 22 mm (0.86 inch) long with:
  a 5 mm (0.197 inch) diameter bone thread 10 mm (0.394 inch) long.
  a 2 mm (0.080 inch) thick, 9.5 mm (0.375 inch) hexagonal wrench feature.
  a 4.7 mm (0.187 inch) diameter, 6.5 mm (0.652 inch) long stud length, and a 10 mm (0.4 inch) thread length.

Dynamized Bone Stabilizer Implanting Method

Referring generally to FIGS. 2, 3 and 4, the plate 30 is attached lateral to the vertebra or bone body 60 with the bone screws 40 through the sliding plate guides tubes 22. The bone screws 40 are threaded into the vertebra or individual bones 60 from a lateral exposure with bicortical purchase. The method is described as a two level fusion involving three adjacent vertebra or individual bone segments with the discs replaced by interbody grafts 62.

First the interbody graft 62 is placed and spinal alignment is confirmed. Next posterior (posterior-lateral) bone screw 40 pilot holes are drilled through a template or drill guide that will ensure proper posterior bone screw 40 alignment, with the adjacent vertebra or individual bone segment's posterior bone screws. Proper posterior bone screw alignment will prevent the plate guide 20 from binding in the plate slot 34. Bone screw 40 pilot hole drilling to direct bone screw placement is well known to those practiced in the art. The pilot holes are tapped with an internal thread and then the posterior screws are placed. Self-tapping bone screws do not require that the pilot hole be tapped. Two posterior bone screws 40 are placed per vertebra or individual bone segments 60. the plate guides 20 are then placed over the posterior bone screws 40 at each segment. The posterior bone screws are adjusted by rotating the bone screw by the middle drive feature 44 or the top drive feature 45 to control the plate guide 20 height. The plate 30 is loaded onto the plate guide tubes 22. The plate guide tubes slidably engage the plate internal slot 34.

The plate 30 is loaded onto the plate guide tubes 22. Plate preloading results in maintenance of construct compression. Each sliding vertebra or individual bone segment's posterior bone screws 40 are then secured firmly to the plate guide tubes 22 with a bone screw-sliding nut 48. The loading is carried out with a compression tool means followed by placement of a stop lock clamp 50, or by subsequent expansion of an expandable interbody means. If needed the stop lock clamp is slid against the plate guide 20 during compression, and then the stop lock clamp is clamped in place, holding the construct in compression. Construct compression techniques and interbody device distraction are well known to those practiced in the art. The outrigger 28 is then secured with the anterior bone screw 47. Each segment screw to be rigidized with respect to the plate 30 is clamped using the bone screw clamp nut 49.

The final adjustment of the plate guide heights are made by loosening the two nuts on the plate guide to be adjusted, then rotating the bone screw with a driving wrench on the top drive feature until the plate guide is at the required level. The wrench should be held while the nuts are being retightened.

Implanting Method Options:

(1) Referring to FIG. 7a, if unidirectional preloaded dynamized action is desired, sliding nuts 48 are threaded onto bone screw 40 and tightened. A compression tool means is used to draw the vertebra or individual bone segments 60 toward each other until the desired preload is reached. This compression prevents motion in the direction of the stop lock clamp 50 to maintain preload as shown in FIGS. 3 and 4.

(2) Referring to FIG. 7b, If rigidizing is desired, clamp nuts 49 are threaded onto bone screw machine threaded stud portion 46 and tightened. The clamp nuts clamp against the plate thereby restricting motion of the plate with the plate guide 20.

We claim:

1. A sliding plate bone stabilizing system, for the purpose of fixing one bone with respect to one or more other bones, comprising:

a. a plate member for placement adjacent to individual bones in a column, said column having a longitudinal bone column axis substantially through the center of said individual bones, said plate having a plate axis essentially parallel to the said bone column axis, said plate axis extending the length of the longest dimension of said plate;

b. said plate having an upper face, a lower face, two substantially parallel side faces, a thickness of sufficient strength to substantially eliminate bending, and a plate through slot substantially parallel to said plate axis; said slot having a width to accommodate attachment devices;

c. a plate guide, said plate guide having two fixed guide tubes configured and sized to slide freely in said slot, said fixed guide tubes having a length greater than the said slot depth so as to protrude above the said plate, and having an outrigger arm with a screw clearance hole in the end of said outrigger arm away from said fixed guide tubes perpendicular to the said plate and said outrigger arm, substantially perpendicular and substantially in the plane of said plate guide;

d. a bone screw, said bone screw having a bone threaded portion, a machine threaded stud portion, and a driving portion between said bone threaded portion, and said bone threaded portion configured and sized to threadably engage said individual bones, and said machine threaded stud portion sized to slidably engage said guide tubes inside diameters, said machine screw to affix said plate to said individual bones;

e. a self tapping anterior bone screw, said anterior bone screw to engage said outrigger threaded hole and threadably engage said individual bones;

f. at least one clamp nut sized and threaded to engage said machine threaded stud portion, and having an undercut center and an outer flange, where said undercut center maintains clearance for said tube protrudance and said outer flange to clamp against said plate upper face.

2. The sliding plate bone stabilizing system of claim 1, further comprising one or more stop lock clamps attached to said plate to control the motion of said plate with respect to said plate guide comprising: a lower stop clamp with a threaded hole, an upper stop clamp with a clearance hole, and a stop screw which passes through said upper stop clearance hole and engages said lower clamp threaded hole.

3. The sliding plate bone stabilizing system of claim 2, wherein one or more of said at least one clamp nut do not contain the said undercut, allowing said one or more of said at least one clamp nut to clamp against said tube allowing said plate to move freely along said plate longitudinal axis with respect to said plate guide.

4. The sliding plate bone stabilizing system of claim 3, further comprising: at least a second plate guide, at least a second bone screw, at least a second nut, at least a second self tapping anterior bone screw.

5. The sliding plate bone stabilizing system of claim 4, with a means for connecting said plate, said plate guides, said bone screws, said clamp nuts, said self tapping anterior bone screws, said upper and lower stop clamp plates, and said stop lock clamps.

6. A method for fixing one or more said bones in a desired relationship, comprising:

a. providing the system of claim 5;

b. placing said bones in a desired relationship;

c. threading said bone screws in said individual bone, spaced at the same distance as said fixed tubes are spaced;
d. sliding a graft means between said individual bones;
e. placing said plate guide tubes over said bone screws and seating said plate guide on said screw driving portion;
f. threading said self tapping anterior screw through, said outrigger hole, into said individual bone;
g. placing said plate over each of said plate guide tubes;
h. threading one of said clamp nuts with said undercut on to each said bone screw machine thread portion that is to be clamped to said plate;
i. threading one of said clamp nuts without said undercut on to each said bone screw machine thread portion that is to move with respect to said plate;
j. tightening said nuts;
k. placing said stop lock in each area needed to control the motion of said plate guides.

7. The sliding plate bone stabilizing system of claim 1, including a graft means, said graft means with sufficient compressive strength to support the weight applied above it and wherein said graft means will substantially restore the original space between the said bones.

* * * * *